United States Patent [19]

Chevallier et al.

[11] Patent Number: 5,932,191
[45] Date of Patent: Aug. 3, 1999

[54] ABRASIVE SILICAS FOR TOOTHPASTE COMPOSITIONS

[75] Inventors: Yvonick Chevallier, Fontaines-Saint-Martin; Adrien Dromard, Lyons, both of France

[73] Assignee: Rhone-Poulenc Chimie, Courbevoie, France

[21] Appl. No.: 08/663,180

[22] PCT Filed: Dec. 28, 1994

[86] PCT No.: PCT/FR94/01543

§ 371 Date: Jul. 31, 1996

§ 102(e) Date: Jul. 31, 1996

[87] PCT Pub. No.: WO95/18066

PCT Pub. Date: Jul. 6, 1995

[30] Foreign Application Priority Data

Dec. 29, 1993 [FR] France .................. 93 15824

[51] Int. Cl.$^6$ .............. A61K 7/16; A61K 7/18; C01B 33/12
[52] U.S. Cl. ............ 424/52; 424/49; 423/335; 423/339
[58] Field of Search .............. 423/339, 335; 424/52, 49

[56] References Cited

U.S. PATENT DOCUMENTS

| 4,243,428 | 1/1981 | Donnet | 106/288 |
|---|---|---|---|
| 4,312,845 | 1/1982 | Wason | 423/339 |
| 4,581,217 | 4/1986 | Shinpo | 423/339 |
| 5,225,177 | 7/1993 | Wason | 423/339 |
| 5,342,598 | 8/1994 | Persello | 423/339 |
| 5,447,704 | 9/1995 | Alddcroft | 423/339 |
| 5,582,816 | 12/1996 | Mandanas | 424/49 |
| 5,603,920 | 2/1997 | Rice | 424/49 |
| 5,624,652 | 4/1997 | Aldcroft | 423/335 |
| 5,651,958 | 7/1997 | Rice | 424/49 |

FOREIGN PATENT DOCUMENTS

| 0139754 | 5/1985 | European Pat. Off. . |
|---|---|---|
| 0236070 | 9/1987 | European Pat. Off. . |
| 0396460 | 11/1990 | European Pat. Off. . |
| 0535943 | 4/1993 | European Pat. Off. . |

*Primary Examiner*—D. Margaret M. Mach
*Attorney, Agent, or Firm*—John Daniel Wood; Jean-Louis Seugnet

[57] ABSTRACT

The present invention relates to silicas, in particular precipitated silicas, which can be used in particular as abrasive agents in toothpaste compositions. The silicas according to the invention have, first of all, low specific surfaces. Their BET specific surface is between 20 and 75 m$^2$/g, preferably between 35 and 64 m$^2$/g. The invention also relates to a process for their preparation and to the toothpaste compositions containing them.

24 Claims, No Drawings

ABRASIVE SILICAS FOR TOOTHPASTE COMPOSITIONS

This application is a 371 of PCT/FR94/01543, filed Dec. 28, 1994.

The present invention relates to silicas, in particular precipitated silicas, which can be used in particular as abrasive agents in toothpaste compositions.

The invention also relates to a process for their preparation and to the toothpaste compositions containing them.

A great many toothpaste compositions have been developed and marketed for several years now.

It is known that toothpaste formulations may contain various components, in particular water, a wetting agent (for example glycerol, sorbitol, xylitol or polyethylene glycol, etc.), a thickener (for example xanthan gum), a source of fluoride (usually sodium fluoride or sodium monofluorophosphate (anti-tooth-decay agent)), a colorant, a flavouring, a sweetener, a fragrance, a preserving agent, a surfactant and/or a therapeutic additive, etc.

They generally also contain an abrasive agent which must, by its mechanical action, remove dental plaque while at the same time not subjecting the teeth themselves to unacceptable abrasion.

Among the abrasive agents usually employed, mention may be made of calcium carbonates and phosphates, sodium metaphosphates, aluminas and, in recent years, silicas.

However, the silicas of the prior art used as abrasive agents in toothpaste compositions are not always of desirable refractive index or porosity.

The aim of the present invention is, in particular, to provide novel silicas of low specific surface, which are, at the same time, of high abrasive power and of relatively low refractive index and oil absorption, these silicas furthermore being compatible with organoamine compounds.

The invention also relates to a process for the preparation of the said silicas and to their use in toothpaste compositions.

Thus, one of the subjects of the invention is a silica, preferably a precipitated silica, which can be used in particular as an abrasive agent in toothpaste compositions, this silica having:

i) a BET specific surface of between 20 and 75 $m^2/g$.

ii) a CTAB specific surface of between 16 and 45 $m^2/g$, iii) an RDA abrasiveness of between 120 and 160, iv) a refractive index of between 1.435 and 1.450, v) a DOP oil absorption of between 70 and 105 ml/100 g, and vi) a compatibility with organoamine compounds, in particular with fluoro amines, of at least 50%.

In the present account, the BET specific surface is determined according to the Brunauer-Emmett-Teller method described in "The Journal of the American Chemical Society", vol. 60, page 309, February 1938 and corresponding to ISO standard 5794/1 (Annex D).

The CTAB specific surface is the external surface determined according to NFT standard 45-007 (November 1987) (5.12).

The RDA ("Radioactive Dentine Abrasion") abrasiveness is measured according to the method described by J. J. Hefferren in "Journal of Dental Research", vol 55(4), page 563, 1976.

According to this method, human teeth irradiated with a flow of neutrons are subjected to a certain amount of mechanical brushing; the abrasive index of the toothpaste tested corresponds to the $^{32}P$ radioactivity emanating from the dentine. A suspension containing 10 grams of calcium pyrophosphate in 50 ml of aqueous 0.5% sodium carboxymethyl cellulose solution is chosen as reference, the RDA of this reference being arbitrarily set at 100. The silica whose RDA it is desired to determine is suspended like the calcium pyrophosphate and subjected to the same mechanical brushing.

The refractive index of the silica in sorbitol is that of the most transparent suspension (and thus that of maximum transmission) of this silica in various water-sorbitol solutions, this transparency being determined by transmission at 589 mm with a spectrophotometer. Each suspension is obtained by dispersion of 1 gram of silica in 19 grams of water-sorbitol solution, followed by de-aeration under gentle vacuum before reading the transmission (reading taken with, as reference product, the silica-free water-sorbitol solution) on the spectrophotometer and the refractive index on a refractometer.

The DOP oil absorption is determined according to ISO standard 787/5 using dioctyl phthalate.

The average size of the silica particles by weight, $D_{50}$, is determined using a Sympatec Helos machine. This machine applies the principle of Fraunhöffer diffraction and uses a low-power He/Ne laser. The sample is predispersed by application of ultrasound in water for 30 seconds in order to obtain an aqueous suspension.

The pH of the silica is measured according to ISO standard 787/9 (pH of a 5% suspension in water).

The compatibility of the silica with bis(hydroxyethyl) aminopropyl-N-(hydroxyethyloctadecylamine) dihydrofluoride, which is a fluoro amine and thus an organoamine compound, is determined in the following manner:

a standard solution containing 1.65% of fluoro amine is prepared by adding 5 g of commercial solution of fluoro amine at a concentration of 33% in propanediol to 95 g of double-distilled water;

an aqueous suspension (or slurry) of silica is formed by dispersion of 6 g of silica in 24 g of standard solution prepared above, and is then kept stirring for 24 hours at 37° C. after adjustment of its pH to 5.0 (by addition of 2N hydrochloric acid);

this suspension is then centrifuged at 10,000 rpm for 30 minutes and the supernatant obtained gives, after filtration on a 0.22 $\mu$m Millipore filter, a solution known as the measurement solution;

the concentration of fluoro amine in the standard solution and in the measurement solution is determined by turbidimetry, in this instance by measuring, with a phototrode set at 550 nm, the turbidity resulting from the formation of micelles between the fluoro amine and an anionic compound (Aerosol OT, consisting of sodium dioctylsulphosuccinate);

the fluoro amine compatibility (FA compatibility) of the silica is given by the ratio $$\frac{\text{concentration of fluoro amine in the measurement solution}}{\text{concentration of fluoro amine in the standard solution}}$$

The silicas according to the invention have, first of all, low specific surfaces.

Their BET specific surface is between 20 and 75 $m^2/g$, preferably between 35 and 64 $m^2/g$ and, for example, between 45 and 59 $m^2/g$; their CTAB specific surface is between 16 and 45 $m^2/g$, preferably between 20 and 40 $m^2/g$ and, for example, between 24 and 36 $m^2/g$.

In general, the difference between the BET specific surface and the CTAB specific surface of the same silica according to the invention is not more than 35 m²/g, for example not more than 25 m²/g.

A high abrasiveness also characterizes the silicas according to the invention: they have an RDA abrasiveness of between 120 and 160, in particular of between 125 and 145.

The refractive index of the silicas according to the invention is relatively low: it is thus between 1.435 and 1.450, preferably between 1.438 and 1.446, for example between 1.440 and 1.444. Thus, they generally have a transmission of greater than 70%, preferably of greater than 75%, or even of greater than 80%.

The silicas according to the invention also have a fairly low DOP oil absorption: this is between 70 and 105 ml/100 g, preferably between 80 and 105 ml/100 g and, more particularly, between 85 and 95 ml/100 g.

The silicas according to the invention are compatible with organoamine compounds, which are often present in toothpaste formulations. The term "organoamine compound" is understood to refer to any active molecule involved in toothpaste formulations and containing at least one nitrogen atom; mention may be made in particular of fluoro amines, used as anti-tooth-decay agents, such as bis(hydroxyethyl) aminopropyl-N-(hydroxyethyloctadecylamine) dihydrofluoride.

The compatibility of the silicas according to the invention with organoamine compounds, in particular with fluoro amines, defined according to the test described above is thus at least 50%, more particularly at least 55%.

Similarly, the silicas according to the invention are generally compatible with metal cations, which are often involved in toothpaste formulations, in particular with metal cations which are divalent and higher and, in particular, zinc, strontium and tin; these cations may be in the form of inorganic salts: mention may be made, for example, of zinc citrate, sulphate or fluoride, strontium chloride and tin fluoride.

The consequence of this compatibility of the silicas according to the invention with organoamine compounds and, in general, with metal cations is that they may, at least to a large extent, fulfil the function initially given to them, which is not often the case with the silicas of the prior art, in particular with so-called abrasive silicas.

In general, they have an average particle size by weight, $D_{50}$, of between 4 and 20 μm, for example between 5 and 12 μm.

The pH of the silicas according to the invention is generally between 6.2 and 7.4.

Another subject of the invention is a process for the preparation of the silica described above, of the type comprising the reaction of a silicate of an alkali metal M with an acidifying agent, by which means a suspension of precipitated silica is obtained, followed by separation and drying of this suspension, characterized in that the precipitation is performed in the following manner:

(i) an initial stock is formed containing part of the total amount of the silicate of alkali metal M employed in the reaction and at least one electrolyte, the concentration of silicate, expressed as $SiO_2$, in the said initial stock being between 35 and 100 g/l and the electrolyte concentration in the said initial stock being between 10 and 40 g/l, (ii) acidifying agent is added to the said initial stock until 50 to 85% of the amount of $M_2O$ present in the said initial stock is neutralized, (iii) acidifying agent and the remainder of the silicate are added simultaneously to the reaction medium, the pH of the reaction medium being maintained between 8.6 and 9.6 during this step (iii), (iv) the addition of silicate is stopped and the addition of the acidifying agent into the reaction medium is continued until a pH value of between 7.0 and 8.0 for the said medium is obtained, (v) the reaction medium then undergoes a first maturation, (vi) acidifying agent is added to the reaction medium until a pH value of between 3.7 and 4.6 for the medium is obtained, (vii) lastly, the reaction medium undergoes a second maturation.

The choice of acidifying agent and of silicate is made in a manner which is well known per se.

A strong inorganic acid such as sulphuric acid, nitric acid or hydrochloric acid, or an organic acid such as acetic acid, formic acid or carbonic acid, is generally used as acidifying agent.

Any common form of silicates, such as metasilicates, disilicates and advantageously a silicate of an alkali metal M in which M is sodium or potassium, may moreover be used as silicate.

In general, sulphuric acid is employed as acidifying agent and sodium silicate as silicate.

In the case where sodium silicate is used, it is generally present in an $SiO_2/Na_2O$ molar ratio of between 2 and 4, more particularly of between 3.0 and 3.8.

As regards more particularly the preparation process according to the invention, precipitation takes place in a specific manner according to the following steps.

A stock which comprises silicate and at least one electrolyte (step (i)) is first formed. The amount of silicate present in the initial stock represents only part of the total amount of silicate employed in the reaction.

As regards the electrolyte, this term is understood here to have its normal definition, that is to say that it means any ionic or molecular substance which, when in solution, decomposes or dissociates to form ions or charged particles. A salt from the group of alkali metal and alkaline-earth metal salts, in particular the metal salt of the starting silicate and of the acidifying agent, for example sodium sulphate in the case of the reaction of a sodium silicate with sulphuric acid, may be mentioned as electrolyte.

The silicate concentration in the initial stock is between 35 and 100 g of $SiO_2$ per liter. This concentration is preferably between 40 and 85 g/l, for example between 45 and 75 g/l.

Similarly, the electrolyte concentration in the initial stock is between 10 and 40 g/l, preferably between 15 and 30 g/l, for example between 19 and 25 g/l.

The second step (step (ii)) consists in adding acidifying agent to the said initial stock until 50 to 85%, preferably 55 to 80%, of the amount of $M_2O$ present in the said initial stock is neutralized.

In a preferred manner, in this second step, the acidifying agent is added to the said initial stock until 60 to 75% of the amount of $M_2O$ present in the said initial stock is neutralized.

The acidifying agent used in this second step and generally also in the rest of the process may be diluted or concentrated; its normality may be between 0.4 and 36 N, for example between 0.6 and 1.5 N.

In particular, in the case where the acidifying agent is sulphuric acid, its concentration is preferably between 40 and 180 g/l, for example between 60 and 150 g/l.

The duration of this second step (step of preneutralization) is usually between 4 and 15 minutes, preferably between 5 and 10 minutes.

Once the desired value for the amount of neutralized $M_2O$ is reached, acidifying agent and the remainder of the silicate are then added simultaneously (step (iii)).

During this simultaneous addition, the pH of the reaction medium is maintained (in particular by controlling the flow rate of acidifying agent) between 8.6 and 9.6, preferably between 9.0 and 9.4, generally at a substantially constant value.

In general, the silicate of an alkali metal M added during this third step has a concentration, expressed as silica, of between 40 and 330 g/l, for example of between 60 and 250 g/l.

The duration of this third step (step of simultaneous addition) is usually between 20 and 90 minutes, preferably between 40 and 75 minutes.

After this step, the addition of silicate is stopped and the addition of the acidifying agent into the reaction medium is continued until a pH value of between 7.0 and 8.0, preferably of between 7.3 and 7.8, for the said medium is obtained (step iv)).

After stopping the addition of acidifying agent, the reaction medium is then allowed to mature for a first time (step (v)), at the pH reached after the above step, preferably for 5 to 30 minutes, for example for 10 to 20 minutes.

This first maturation generally takes place under hot conditions, preferably at a constant temperature of between 75 and 98° C., and usually with stirring.

Next, after the said maturation, further acidifying agent is added to the reaction medium until a pH value of between 3.7 and 4.6, preferably of between 3.9 and 4.5, for the said medium is obtained (step (vi)).

After stopping the addition of acidifying agent, the reaction medium is then left to mature for a second time (step (vii)), at the pH reached after the above step, preferably for 5 to 30 minutes, for example for 10 to 20 minutes.

This second maturation also generally takes place under hot conditions, preferably at a temperature of between 75 and 98° C., and usually with stirring.

The same acidifying agent is generally used throughout the preparation process according to the invention.

During the reaction (steps (i) to (vii)), the temperature of the reaction medium is generally between 75 and 98° C., preferably between 85 and 95° C.; this temperature is usually maintained at a substantially constant value during steps (i) to (vii).

After the operations which have just been described, a silica broth is obtained, which is then separated (liquid-solid separation). This separation generally consists of a filtration, followed if necessary by washing. The filtration may be performed according to any suitable method, for example using a rotary filter under vacuum.

The silica suspension thus recovered (filtration cake) is then dried.

This drying is preferably performed by spraying.

To this end, any suitable type of spraying device may be used, in particular a spraying device with turbines, with nozzles, with liquid pressure or with two fluids; a turbine spraying device is advantageously used.

It should be noted that the cake to be dried is not always under conditions which allow spraying on account of its excessively high viscosity.

In a manner which is known per se, the cake is then subjected to a crumbling operation. This operation may be performed by passing the cake into a mill of colloidal or ball type (fluidification by mechanical action).

After the drying, a step of grinding may be carried out on the product recovered in order to obtain the desired particle size; a blade or hammer mill or an air-jet mill may be employed in particular.

Lastly, the invention relates to toothpaste compositions containing at least one silica of the type described above or obtained by the process which has just been outlined.

The silicas according to the invention or prepared according to the process of the invention find, in point of fact, a particularly advantageous application as abrasive agents in toothpastes in which they are incorporated.

The amount of silica according to the invention or prepared according to the process of the invention, used in toothpaste compositions, may vary within a wide range; it is generally between 5 and 40% by weight, for example between 5 and 25% by weight.

Toothpastes containing the silicas according to the invention or prepared according to the process of the invention preferably have a very satisfactory cleaning power. Furthermore, the production of translucent toothpastes containing the said silicas is possible.

Lastly, on account of the relatively low refractive index (combined with a fairly high transmission) of the silica according to the invention, the amount of conventional wetting agent to be incorporated into a toothpaste composition containing the said silica may be reduced and partly replaced by water, thereby leading to a decrease in the cost of the final product.

The examples which follow illustrate the invention without, however, limiting the scope.

EXAMPLE 1

The following are introduced into a 2000-liter stainless steel reactor fitted with a helical stirring system, a system for introduction of the reactants and a system of heating via a jacket:

117 liters of a sodium silicate solution of $SiO_2/Na_2O$ molar ratio equal to 3.6, having a concentration, expressed as silica, of 136 g/l and being at a temperature of 65° C., 80 liters of an aqueous solution containing 4.0 kg of $Na_2SO_4$ (electrolyte).

The concentration of silicate, expressed as $SiO_2$, and that of electrolyte in the initial stock are thus, respectively, 80.7 g/l and 20.3 g/l. The mixture obtained is brought to a temperature of 92° C. while at the same time keeping it stirred. The entire reaction is carried out at 92° C.

A sulphuric acid solution, of concentration equal to 80 g/l, is first introduced at a flow rate of 7.6 l/min over 8 min into the stock thus formed and kept stirring; after this addition, the degree of neutralization of the stock is 67%, that is to say that 67% of the amount of $Na_2O$ present in the initial stock is neutralized.

The following are then introduced simultaneously, for 60 min, into the reaction medium:

a sodium silicate solution as described above (concentration, expressed as silica, of 136 g/l), at a flow rate of 12 l/min, and a sulphuric acid solution as described above (concentration of 80 g/l) at a flow rate controlled such that the pH of the reaction medium is equal to 9.2 during this simultaneous addition.

The introduction of the sodium silicate solution is then stopped but the addition of the sulphuric acid solution is continued, at a flow rate of 7.6 l/min, until the pH of the reaction medium is equal to 7.5.

The introduction of the sulphuric acid solution is then stopped and the reaction medium is left to mature for 15 min, at a pH of 7.5 (with stirring, at 92° C.).

Further sulphuric acid solution as described above (concentration of 80 g/l) is then introduced, at a flow rate of 7.6 l/min, until the pH of the reaction medium is equal to 4.2.

The introduction of the sulphuric acid solution is then stopped and the reaction medium is left to mature for 15 min, at a pH of 4.2 (with stirring, at 92° C.).

A precipitated silica broth is thus obtained, which is filtered and washed by means of a rotary filter under vacuum.

The silica cake obtained is then fluidified by simple mechanical action. After this crumbling operation, the resulting broth is sprayed using a turbine spraying device; lastly, the dried product is ground.

The characteristics of the precipitated silica S1 thus prepared are collated in Table 1.

EXAMPLE 2

The following are introduced into a 2000-liter stainless steel reactor fitted with a helical stirring system, a system for introduction of the reactants and a system of heating via a jacket:

67 liters of a sodium silicate solution of $SiO_2/Na_2O$ molar ratio equal to 3.6, having a concentration, expressed as silica, of 136 g/l and being at a temperature of 65° C.,
113 liters of an aqueous solution containing 4.5 kg of $Na_2SO_4$ (electrolyte).

The concentration of silicate, expressed as $SiO_2$, and that of electrolyte in the initial stock are thus, respectively, 50.6 g/l and 25.0 g/l. The mixture obtained is brought to a temperature of 92° C. while at the same time keeping it stirred. The entire reaction is carried out at 92° C.

A sulphuric acid solution, of concentration equal to 80 g/l, is first introduced at a flow rate of 7.6 l/min over 5 min into the stock thus formed and kept stirring; after this addition, the degree of neutralization of the stock is 73%, that is to say that 73% of the amount of $Na_2O$ present in the initial stock is neutralized.

The following are then introduced simultaneously, for 75 min, into the reaction medium:

a sodium silicate solution as described above (concentration, expressed as silica, of 136 g/l), at a flow rate of 12 l/min, and
a sulphuric acid solution as described above (concentration of 80 g/l) at a flow rate controlled such that the pH of the reaction medium is equal to 8.9 during this simultaneous addition.

The introduction of the sodium silicate solution is then stopped but the addition of the sulphuric acid solution is continued, at a flow rate of 7.6 l/min, until the pH of the reaction medium is equal to 7.2.

The introduction of the sulphuric acid solution is then stopped and the reaction medium is left to mature for 15 min, at a pH of 7.2 (with stirring, at 92° C.).

Further sulphuric acid solution as described above (concentration of 80 g/l) is then introduced, at a flow rate of 7.6 l/min, until the pH of the reaction medium is equal to 4.2.

The introduction of the sulphuric acid solution is then stopped and the reaction medium is left to mature for 15 min, at a pH of 4.2 (with stirring, at 92° C.).

A precipitated silica broth is thus obtained, which is filtered and washed by means of a rotary filter under vacuum.

The silica cake obtained is then fluidified by simple mechanical action. After this crumbling operation, the resulting broth is sprayed using a turbine spraying device; lastly, the dried product is ground.

The characteristics of the precipitated silica S2 thus prepared are collated in Table 1.

EXAMPLE 3

The following are introduced into a 2000-liter stainless steel reactor fitted with a helical stirring system, a system for introduction of the reactants and a system of heating via a jacket:

115 liters of a sodium silicate solution of $SiO_2/Na_2O$ molar ratio equal to 3.6, having a concentration, expressed as silica, of 136 g/l and being at a temperature of 65° C.,
85 liters of an aqueous solution containing 4.0 kg of $Na_2SO_4$ (electrolyte).

The concentration of silicate, expressed as $SiO_2$, and that of electrolyte in the initial stock are thus, respectively, 78.2 g/l and 20.0 g/l. The mixture obtained is brought to a temperature of 90° C. while at the same time kept stirring. The entire reaction is carried out at 90° C.

A sulphuric acid solution, of concentration equal to 80 g/l, is first introduced at a flow rate of 7.6 l/min over 7 min into the stock thus formed and kept stirring; after this addition, the degree of neutralization of the stock is 60%, that is to say that 60% of the amount of $Na_2O$ present in the initial stock is neutralized.

The following are then introduced simultaneously, for 60 min, into the reaction medium:

a sodium silicate solution as described above (concentration, expressed as silica, of 136 g/l), at a flow rate of 12 l/min, and
a sulphuric acid solution as described above (concentration of 80 g/l) at a flow rate controlled such that the pH of the reaction medium is equal to 9.2 during this simultaneous addition.

The introduction of the sodium silicate solution is then stopped but the addition of the sulphuric acid solution is continued, at a flow rate of 7.6 l/min, until the pH of the reaction medium is equal to 7.5.

The introduction of the sulphuric acid solution is then stopped and the reaction medium is left to mature for 15 min, at a pH of 7.5 (with stirring, at 92° C.).

Further sulphuric acid solution as described above (concentration of 80 g/l) is then introduced, at a flow rate of 7.6 l/min, until the pH of the reaction medium is equal to 4.2.

The introduction of the sulphuric acid solution is then stopped and the reaction medium is left to mature for 15 min, at a pH of 4.2 (with stirring, at 92° C.).

A precipitated silica broth is thus obtained, which is filtered and washed by means of a rotary filter under vacuum.

The silica cake obtained is then fluidified by simple mechanical action. After this crumbling operation, the resulting broth is sprayed using a turbine spraying device; lastly, the dried product is ground.

The characteristics of the precipitated silica S3 thus prepared are collated in Table 1.

EXAMPLE 4

The following are introduced into a 2000-liter stainless steel reactor fitted with a helical stirring system, a system for introduction of the reactants and a system of heating via a jacket:

117 liters of a sodium silicate solution of $SiO_2/Na_2O$ molar ratio equal to 3.6, having a concentration, expressed as silica, of 136 g/l and being at a temperature of 65° C., 80 liters of an aqueous solution containing 4.0 kg of $Na_2SO_4$ (electrolyte).

The concentration of silicate, expressed as $SiO_2$, and that of electrolyte in the initial stock are thus, respectively, 80.7 g/l and 20.3 g/l. The mixture obtained is brought to a temperature of 92° C. while at the same time kept stirring. The entire reaction is carried out at 92° C.

A sulphuric acid solution, of concentration equal to 80 g/l, is first introduced at a flow rate of 8.4 l/min over 7 min into the stock thus formed and kept stirring; after this addition, the degree of neutralization of the stock is 65%, that is to say that 65% of the amount of $Na_2O$ present in the initial stock is neutralized.

The following are then introduced simultaneously, for 60 min, into the reaction medium:

a sodium silicate solution as described above (concentration, expressed as silica, of 136 g/l), at a flow rate of 13.2 l/min, and a sulphuric acid solution as described above (concentration of 80 g/l) at a flow rate controlled such that the pH of the reaction medium is equal to 9.2 during this simultaneous addition.

The introduction of the sodium silicate solution is then stopped but the addition of the sulphuric acid solution is continued, at a flow rate of 7.6 l/min, until the pH of the reaction medium is equal to 7.5.

The introduction of the sulphuric acid solution is then stopped and the reaction medium is left to mature for 15 min, at a pH of 7.5 (with stirring, at 92° C.).

Further sulphuric acid solution as described above (concentration of 80 g/l) is then introduced, at a flow rate of 7.6 l/min, until the pH of the reaction medium is equal to 4.2.

The introduction of the sulphuric acid solution is then stopped and the reaction medium is left to mature for 15 min, at a pH of 4.2 (with stirring, at 92° C.).

A precipitated silica broth is thus obtained, which is filtered and washed by means of a rotary filter under vacuum.

The silica cake obtained is then fluidified by simple mechanical action. After this crumbling operation, the resulting broth is sprayed using a turbine spraying device; lastly, the dried product is ground.

The characteristics of the precipitated silica S4 thus prepared are collated in Table 1.

TABLE 1

|  | S1 | S2 | S3 | S4 |
|---|---|---|---|---|
| BET specific surface ($m^2/g$) | 35 | 23 | 54 | 29 |
| CTAB specific surface ($m^2/g$) | 24 | 22 | 28 | 19 |
| RDA | 135 | 140 | 120 | 147 |
| Refractive index | 1.446 | 1.442 | 1.444 | 1.444 |
| Transmission at this index (%) | 83 | 83 | 78 | 88 |
| DOP oil absorption (ml/100 g) | 98 | 74 | 105 | 95 |
| Average size by weight $D_{50}$ ($\mu m$) | 5.4 | 8.0 | 5.0 | 4.2 |

TABLE 1-continued

|  | S1 | S2 | S3 | S4 |
|---|---|---|---|---|
| pH | 6.2 | 6.3 | 6.4 | 6.2 |
| FA compatibility (%) | 56 | 58 | 55 | 61 |

What is claimed is:

1. A silica having:
   i) a BET specific surface of between 20 and 75 $m^2g$,
   ii) a CTAB specific surface of between 16 and 45 $m^2g$,
   iii) an RDA abrasiveness of between 125 and 145,
   iv) a refractive index of between 1.435 and 1.450,
   v) a DOP oil absorption of between 70 and 105 ml/100 g, and
   vi) a compatibility with organoamine compounds.

2. A silica according to claim 1 wherein the BET specific surface is between 35 and 64 $m^2/g$.

3. A silica according to claim 2 wherein the BET specific surface is between 45 and 59 $m^2/g$.

4. A silica according to claim 1 wherein the CTAB specific surface is between 20 and 40 $m^2/g$.

5. A silica according to claim 1 wherein the refractive index is between 1.438 and 1.446.

6. A silica according to claim 1 wherein the DOP oil absorption is between 80 and 105 ml/100 g.

7. A silica according to claim 1 wherein the compatibility with organoamine compounds is at least 55%.

8. A silica according to claim 1 wherein the organoamine compounds are fluoro amines.

9. A silica according to claim 1 wherein the transmission is greater than 70%.

10. A silica according to claim 1 wherein the average particle size by weight, $D_{50}$, is between 4 and 20 $\mu m$.

11. A silica according to claim 1 wherein the pH of a 5% suspension of water of said silica is between 6.2 and 7.4.

12. A silica according to claim 1 wherein the difference between the BET specific surface and the CTAB specific surface is not more than 35 $m^2/g$.

13. A silica according to claim 12 wherein the difference is no more than 25 $m^2/g$.

14. A silica according to claim 1 being a precipitated silica.

15. A process for the preparation of the silica of claim 1 comprising the reaction of a silicate of an alkali metal M with an acidifying agent, by which means a suspension of precipitated silica is obtained, followed by separation and drying of this suspension wherein the precipitation is performed in the following manner:

(i) forming an initial stock containing part of the total amount of the silicate employed in the reaction and at least one electrolyte, the concentration of silicate, expressed as $SiO_2$, and the electrolyte concentration in the said initial stock respectively being between 35 and 100 g/l and between 10 and 40 g/l, (ii) adding an acidifying agent to said initial stock until 50 to 85% of the amount of M, calculated as $M_2O$, present in the said initial stock is neutralised, (iii) adding the remainder of the silicate and additional acidifying agent simultaneously to the reaction medium, the pH of the reaction medium being maintained between 8.6 and 9.6 during this step (iii), (iv) stopping the addition of silicate while continuing the addition of acidifying agent into the reaction medium until a pH value of between 7.0 and 8.0 for the said medium is obtained then, (v) allowing the reaction medium to undergo to a first maturation, (vi) adding acidifying agent to the reaction medium until a pH value of between 3.7 and 4.6 for the said medium is obtained, and (vii) lastly, allowing the reaction medium to undergo a second maturation.

16. A process according to claim 15 wherein, during step (iii), the pH of the reaction medium is maintained between 9.0 and 9.4.

17. A process according to claim 15 wherein, during step (iv), the acidifying agent is added until a pH value of between 7.3 and 7.8 for the reaction medium is obtained.

18. A process according to claim 15 wherein the durations of steps (v) and (vii) are each between 5 and 30 minutes.

19. A process according to claim 16 wherein the temperature of the reaction medium is maintained at a substantially constant temperature, of between 75 and 98° C., during steps (i) to (vii).

20. A process according to claim 15 wherein the drying of said suspension is carried out by spraying.

21. A process according to claim 15 wherein, after the drying, the product obtained is ground.

22. A toothpaste composition comprising an effective abrasive amount of a silica as defined in claim 1.

23. A toothpaste composition of claim 22 comprising between 5 and 40% by weight of said silica.

24. A toothpaste composition of claim 22 comprising between 5 and 25% by weight of said silica.

\* \* \* \* \*